United States Patent
Tisinger et al.

(10) Patent No.: US 6,818,211 B2
(45) Date of Patent: Nov. 16, 2004

(54) GRAM-POSITIVE FATTY ACID DEGRADER

(75) Inventors: Jessi Lind Tisinger, Floyd, VA (US);
Domenic A. Paone, Roanoke, VA (US);
Jonathan Leder, Montvale, VA (US);
David J. Drahos, Roanoke, VA (US)

(73) Assignee: Novozymes Biologicals, Inc.

( * ) Notice: Subject to any disclaimer, the term of this patent is extended or adjusted under 35 U.S.C. 154(b) by 336 days.

(21) Appl. No.: 10/128,050

(22) Filed: Apr. 23, 2002

(65) Prior Publication Data

US 2003/0008382 A1 Jan. 9, 2003

Related U.S. Application Data

(63) Continuation-in-part of application No. 09/861,142, filed on May 18, 2001, now Pat. No. 6,649,401.

(51) Int. Cl.$^7$ .............................................. A01N 63/00
(52) U.S. Cl. ................. 424/93.46; 435/198; 435/252.4; 435/244; 424/93.3
(58) Field of Search ............................. 424/93.46, 93.3; 435/198, 252.4, 244

(56) References Cited

U.S. PATENT DOCUMENTS 6,066,494 A * 5/2000 Hsieh et al. ................. 435/263

* cited by examiner

*Primary Examiner*—Irene Marx
(74) *Attorney, Agent, or Firm*—Mishrilal Jain (57) ABSTRACT

The invention discloses a Gram-positive microorganism, *Bacillus megaterium* that effectively and efficiently degrades fats, oils and grease. A composition comprising said microorganism and a method for degrading fatty acids and grease are also disclosed. Availability of glycerol to the biodegrading microorganism was discovered to enhance biodegradation.

4 Claims, 7 Drawing Sheets

Figure 1. The efficacy of SB3112 and various microorganisms to degrade grease.

Figure 2. The effect of glycerol on the biodegrading activity of SB3112.

Figure 3. The effect of a serial dilution of Glycerol on the degradation of Palmitic Acid (PA).

Figure 4. Degradation of various amounts of Glycerol by SB3112 without the presence of Palmitic Acid.

Figure 5. The oxygen uptake attributed to the degradation of Palmitic Acid with the glycerol oxygen uptake subtracted out. The legend shows the original amount of glycerol present.

Figure 6. Various strains of *Bacillus megaterium* were tested for the degradation of Palmitic Acid in the presence of Glycerol.

Figure 7. Commercially available product versus SB3112 product for the degradation of Palmitic Acid (PA) in the presence of Glycerol. Glycerol only treatments are also shown.

GRAM-POSITIVE FATTY ACID DEGRADER

This is a continuation in part of pending U.S. application Ser. No. 09/861,142 filed May 18, 2001, now U.S. Pat. No. 6,649,401.

FIELD OF THE INVENTION

The present invention is related to identifying a Gram-positive organism that degrades fats, oils and grease. More particularly, the present invention is related to providing a non-pathogenic, spore-forming Gram-positive, lipophilic bacterial strain that produces extracellular lipase and also efficiently oxidizes or degrades fatty acids and grease. The invention is further related to a liquid and dry formulations comprising said Gram-positive organism and a method for enhancing fatty acid degradation employing glycerol.

BACKGROUND

Most food service establishments are required to have a device that prevents grease from flowing directly from the kitchen or food preparation area into the sewer or to an on-site waste disposal system. Commonly called grease traps, these devices function to physically prevent oils and grease from flowing directly into the sanitary sewer and to store the separated grease solid for eventual solid waste disposal.

Many municipalities place restrictions and surcharges based on the biological oxygen demand (BOD) and oil and grease (O&G) levels in the effluents from grease traps. In addition to wastewater treatment costs and surcharges, the grease solids from the traps must also be periodically removed and disposed. The food service establishment then faces two recurring charges for wastewater treatment, one a municipal treatment cost and secondly a grease disposal cost.

However, the frequency of pumping the accumulated grease solids can be quite variable, ranging from several weeks to several months. If traps are not cleaned on a regular basis, grease clogs may occur causing wastewater to back up into the food preparation area causing malodors and requiring the establishment to close until the problem is corrected. In addition to providing physical means to trap O&G, grease traps can function to biologically mediate a reduction of BOD and O&G in the bulk liquid resulting in cleaner effluent wastewater. This reduction of BOD and O&G is dependent upon the hydraulic retention time, which is dependent on the size of the grease trap and wastewater flow. Other factors that affect biological activity within a grease trap include pH, temperature and whether or not the facility practices bioaugmentation.

Bioaugmentation, the addition of commercial bacterial products that increase the biological activity in the system, has been used to reduce the BOD and O&G in the effluents from grease traps. This has helped to reduce surcharges that the food establishments must pay to municipalities for wastewater services. Additionally, bioaugmentation has been used to decrease the pumping frequency of grease traps, to keep drain lines open and to reduce malodors.

In addition to grease traps, bioaugmentation has also been used to help remove grease from lift stations, drain lines, septic tanks, waste treatment facilities and other situations where grease accumulation can cause flow problems and malodors.

Bioaugmentation products can be either liquid or dry. Because of ease of handling, liquid products are generally preferred and can be added by a liquid metering pump drawing on a container that is replenished on a periodic basis. However, dry formulations are preferred for other applications such as waste treatment facilities.

Strains used in bioaugmentation of grease applications produce an important extracellular enzyme, lipase. This enzyme hydrolyzes and breaks the ester bond between the glycerol backbone and the fatty acid moieties making up the grease. The glycerol is quickly disposed by biodegradation. However, the fatty acids are difficult to degrade and can persist causing pH drops, clogging and malodors.

When Gram-negative microorganisms are used for bioaugmentation in liquid products, they are present as vegetative cells and as such, they may be killed by chemicals, such as surfactants and preservatives, which are often used in such formulations. Therefore, products containing Gram-negative organisms cannot contain biocides and surfactants. Then, unpreserved liquid products may develop severe malodors from microbial contaminants growing in the product. Some of these contaminants may be undesirable in a food service environment. Furthermore, unpreserved products may also suffer from decreased shelf life and efficacy. Clearly, while Gram-negative microorganisms have an advantage in fatty acid degradation, their use in residential and food service products have serious drawbacks.

Dry Gram-negative products, on the other hand, do have an advantage of improved shelf life over liquid Gram-negative formulations. However, this advantage is modest and varies significantly from bacterial strain to bacterial strain in the product. Although dry products can be rehydrated with water and applied like liquid products, the disadvantages of using unpreserved liquids containing Gram-negative microorganisms still apply to rehydrated dry materials.

Many Gram-negative microorganisms are known to have the ability to biodegrade fatty acids generated by the action of lipase. This ability to oxidize and degrade fatty acids is generally not found in Gram-positive spore-forming microorganisms, specifically members of the genus *Bacillus*.

Accordingly, there is a need to develop bioaugmentation formulations that can effectively and efficiently degrade or oxidize fats, oil and grease without causing malodors or other undesirable conditions, such as occurs with Gram-negative organisms.

Specifically, there is a need to find non-pathogenic, spore-forming Gram-positive, lipophilic bacterial strain that produces extracellular lipase and efficiently oxidizes or breaks down fatty acids and grease. Heretofore, such a Gram-positive organism and a formulation containing the same have not been identified or produced.

If fatty acid degrading microorganisms are identified, there is a further need to augment or enhance the fatty acid degrading activity of such microorganisms in order to maximize the effectiveness of products based thereon.

SUMMARY OF THE INVENTION

It is, therefore, an object of the present invention to provide a non-pathogenic, spore-forming Gram-positive, lipophilic bacterial strain that produces extracellular lipase and also efficiently hydrolyzes or degrades fatty acids and grease or a mixture of fatty acid and grease.

It is a further object of the present invention to provide liquid and dry compositions comprising a non-pathogenic, spore-forming Gram-positive, lipophilic bacterial strain that produces extracellular lipase and efficiently hydrolyzes or degrades fats, oils and grease.

An additional object of the present invention is to provide a method for degrading fatty acid and grease using a Gram-positive strain of *Bacillus* species.

Yet another object of the present invention is to enhance the biodegrading activity of Gram-positive strain of *Bacillus* species.

A further object of the invention is to provide a method for augmenting fatty acid degrading activity of microorganisms employing glycerol as an activity enhancer.

Various other objects and advantages of the present invention will become evident from a brief description of the drawings and detailed description of the invention.

Additional advantages and novel features of the invention will be set forth in part in the description that follows, and in part will become more apparent to those skilled in the art upon examination of the following or upon learning by practice of the invention.

DETAILED DESCRIPTION OF THE INVENTION

The above and various other objects and advantages of the present invention are achieved by a biologically pure culture of a Gram-positive microorganism, *Bacillus megaterium*, strain SB3112, having the identifying characteristics of American Type Culture Collection, 10801 University Boulevard, Manassas, Va. 20110-2209, deposit number PTA-3142, and a composition comprising the same. The deposit shall be maintained in viable condition at the ATCC during the entire term of the issued patent and shall be made available to any person or entity for non-commercial use without restriction, but in accordance with the provisions of the law governing the deposit.

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

The term "biodegradation", "biodegraded", or "biodegrading" as used herein means that the substrate is broken down, oxidized or degraded by the microorganism. And the term "activity enhancement" as used herein means that the biodegradation activity of the microorganism is increased by the presence or addition of a particular component, said component being designated as "activity enhancer", or "activator".

By utilizing a Gram-positive, spore-forming organism that can oxidize fatty acids, one can obtain the advantages of an improved preserved liquid product, and stable, easy to use dry products. Unlike Gram-negative containing products, the preserved, spore-based Gram-positive containing product can contain preservatives and surfactants to aid in the biodegradation of fats, oils or grease, because the spores are relatively resistant to biocides and surfactants. Furthermore, these products may also contain micronutrients promoting the growth of the microorganisms. Thus, a Gram-positive product comprising lipase producing, fatty acid degrading, spore-forming microorganism in a preserved liquid formulation offers various advantages required for efficacious degradation of oil and grease. Dry products also benefit from the activity of SB3112.

Liquid and dry products formulated in accordance with the present invention for grease traps, or other similar uses where fatty acid or grease needs to be degraded, may also contain in addition to surfactants, biocides, growth promoting non-toxic amounts of inorganic nutrients and micronutrients, certain activity enhancers, stabilizers, viscosifiers, enzymes, fillers, preservatives and the like. Table 1 lists examples of various components that a liquid formulation may contain in addition to SB3112 in accordance with the present invention.

Other inclusions in both liquid and dry formulations are exemplified below:

(A) Other microorganisms may be selected from the group consisting of the genera *Acinetobacter, Aspergillus, Azospirillum, Burkholdena, Bacillus, Ceriporiopsis, Enterobacter, Escherichia, Lactobacillus, Paenebacillus, Paracoccus, Pseudomonas, Rhodococcus, Syphingomonas, Streptococcus, Thiobacillus, Trichoderma,* and *Xanthomonas*.

(B) Within *Bacillus* genera, the microorganism may be selected from the group consisting of *Bacillus licheniformis, Bacillus subtilus, Bacillus amyoliquofaciens, Bacillus laevolacticus,* and *Bacillus pasteurii* and *Bacillus megaterium* other than strain SB3112 and a combination thereof. The preservative is selected from the group consisting of 1,2-benzisothiazolin-3-one;5-chloro-2-methyl-4-isothiazolin-3-one, 2-methyl-4-isothiazolin-3-one; quaternium-15; phenol; sodium o-phenylphenate; o-phenylphenol; 6-acetoxy-2,4-dimethyl-m-dioxane; chlorhexidine; tris(hydroxymethyl)nitromethane; hexahydro-1,3,5-tris(2-hydroxyethyl)-s-triazine; p-hydroxybenzoic acid or its methyl, ethyl, propyl, or butyl esters; benzoic, ascorbic, citric, or sorbic acid; imidazolidinyl urea; diazolidinyl urea; dimethylol dimethylhydantoin; methylene bisthiocyanate; 2-bromo-2-nitropropane-1,3-diol; 1,2-benzisothiazoline-3-one; methyl anthranilate and a mixture thereof.

(C) The surfactant is selected from the group consisting of trideceth-3; 3 mole ethylene oxide adduct of a linear, primary C12–14 alcohol; 7 mole ethylene oxide adduct of a linear, primary C12–14 alcohol; sodium lauryl sulfate; ammonium lauryl sulfate; dodecyl benzene sulfonic acid; ammonium lauryl sulfate; sodium xylene sulfonate; sodium lauryl sulfate; cocamide diethanolamine; lauramine oxide; sodium alphasulfo methyl C12–18 ester and disodium alphasulfo C12–18 fatty acid salt; sodium dodecylbenzene sulfonate; alkyl polyglycoside; nonylphenoxypoly (ethyleneoxy) ethanol, branched; nonylphenoxypoly (ethyleneoxy) ethanol, branched; alkoxylated linear alcohol; blend of ethoxylates of linear, primary 12–14 carbon number alcohol; linear alkyl sulfate; alkanolamide; octylphenoxypolyethoxyethanol absorbed on magnesium carbonate; sodium dodecylbenzene sulfonate and isopropyl alcohol; poe (6) tridecyl alcohol; poly (oxy-1,2-ethanediyl), alpha (nonylphenyl)-omega hydroxy, branched, or other surfactants known in the art, and a mixture thereof.

(D) The nutrients are selected from the group consisting of disodium phosphate, monosodium phosphate, sodium thiosulfate, ammonium sulfate, magnesium sulfate, manganese sulfate, ferrous sulfate, potassium phosphate, dipotassium phosphate, monocalcium phosphate, magnesium chloride, calcium chloride, chelated iron, manganese chloride, sodium molybdate, cobalt chloride, sodium nitrate, bakers yeast, yeast extract, soy peptone, skim milk powder, beef extract, sarsaponin, whey, gelatin, and urea and others known in the art, and a mixture thereof.

(E) The dry fillers are selected from the group consisting of starch, sodium chloride, glucose, sodium bicarbonate, corncobs, bran, and various ground grains.

(F) The enzymes are selected from the group consisting of protease, amylase, lipase and cellulase and others known in the art, and a mixture thereof.

(G) The range (w/w) in which various components may be included in the dry product composition in accordance with the present invention are as follows:
(i) SB3112 ranging from about $1 \times 10^5$ to about $5 \times 10^{11}$ CFU/g
(ii) glycerol ranging from about 0 to about 10%
(iii) surfactant ranging from 0 to 10%
(iv) enzymes ranging from 0 to 1%
(v) preservative ranging from 0 to 1.0%
(vi) nutrients ranging from about 0 to 20%
(vii) filler ranging from 0 to 95%

(H) The range (w/v) in which various components may be included in the liquid product composition in accordance with the present invention are as follows:
(i) SB3112 ranging from about $1 \times 10^5$ to about $5 \times 10^{11}$ CFU/ml
(ii) glycerol ranging from about 0 to about 10%
(iii) surfactant ranging from 0 to 10%
(iv) preservative ranging from 1 ppm to 1.0%
(v) color ranging from 0 to 1%
(vi) fragrance ranging from 0 to 1.0%
(vii) viscosifier ranging from 0 to 5%
(viii) nutrients ranging from 0 to 20%
(ix) enzymes ranging from 0 to 1%

Superiority of SB3112

In order to show unexpectedly significant superiority of SB3112 over other *Bacillus megaterium* strains, the following side-by-side comparative study was performed using three other *Bacillus megaterium* strains having designations Strain 1, Strain 2 and Strain 3. Stearic acid (SA) and glycerol (G) were used as substrates. Stearic acid degradation was determined by standard respirometric (oxygen uptake) measurement and sterile techniques were used in all studies.

A CES AER-200 respirometer unit was used. The 500 ml respirometer bottles contained $SSC_3$ minimal salt medium and 20 mM MOPS adjusted to pH 7.2. Respirometer bottles were prepared by adding $SSC_3$ mineral salt media to each bottle. This media contained the following chemicals per liter of water: $NH_4Cl$, 0.8 g; $MgSO_4 \cdot 7H_2O$, 0.2 g; $CaCl_2 \cdot 2H_2O$, 10 mg; $Fe_2Na_2$Ethylene diamine tetraacetic acid, 15 mg; $KH_2PO_4$, 3.06 g; $FeSO_4 \cdot 7H_2O$, 28 µg; $ZnSO_4 \cdot 7H_2O$, 140 µg; $MnSO4 \cdot H_2O$, 84 µg; $CoCl_2 \cdot 6H_2O$, 24 µg; $CuSO_4 \cdot 5H_2O$, 25 µg; $NaMoO_4 \cdot 2H_2O$, 24 µg. The buffer, 3-(N-morpholino) propane sulfonic acid (MOPS), was added 4.28 g per liter. The pH of the medium was adjusted to 7.0 prior to autoclaving. The bottles containing $SSC_3$ media were autoclaved for two hours.

The target substrate, 1000 ppm stearic acid (SA), was added as indicated below. The SA was weighed and added individually into the appropriate reactor prior to autoclaving. Glycerol, 500 ppmv, was added to all bottles. Glycerol was first diluted 50% v/v with deionized water to reduce the viscosity and 0.5 ml was added to each reactor prior to autoclaving. A pure culture of microorganism was used as inoculum. The optical density (OD) of an overnight culture in plate count broth (PCB) was determined in order to estimate the bacterial count. The target dose into each reactor was $1 \times 10^6$ CFU/ml based on the optical density measurement of the broth culture. Following inoculation, a caustic trap containing 5 ml of 30% KOH to remove carbon dioxide was suspended in the bottle and the septum cap was secured tightly. MacConkey streaks were performed on the inoculum prior to its use to ensure the absence of Gram-negative contamination MacConkey and standard methods agar (SMA) plate streaks were also performed on each bottle's contents at the end of the experiment (MacConkey agar plates were used to detect Gram-negative contamination; SMA plates were used to test for pure cultures).

The Treatments (in duplicate) were as follows:
Glycerol+SB3112
Glycerol+Stearic acid+SB3112
Glycerol+Strain 1
Glycerol+Stearic acid+Strain 1
Glycerol+Strain 2
Glycerol+Stearic acid+Strain 2
Glycerol+Strain 3
Glycerol+Stearic acid+Strain 3

As indicated above, all cultures were tested with stearic acid plus glycerol. A glycerol only control was also monitored for each individual strain.

The values for stearic acid degradation lag phase, oxygen uptake rate, and the total cumulative oxygen uptake for each strain are presented in Table 2. These oxygen uptake rates were calculated using a three-point average and the maximum values are shown The data clearly indicate surprising results, showing that SB3112 is superior, demonstrating the highest activity on stearic acid by having the shortest lag phase, the fastest uptake rate and the greatest cumulative oxygen uptake, compared to all other strains tested.

Efficacy of SB3112 for Degrading Various Fatty Acids

Having determined the superiority of SB3112 compared to other *Bacillus megaterium* strains, the following study was performed to determine the efficacy of SB3112 for degrading fatty acids. For this purpose, a number of fatty acids (99% or greater purity) were obtained from commercial sources as listed below:
oleic acid, C-18:1
stearic acid, C-18
palmitic acid, C-16
valeric acid, C-5
butyric acid, C-4
acetic acid, C-2

Respirometric (oxygen uptake) activity was used to measure the ability of SB3112 to degrade fatty acids.

A CES AER-200 respirometer unit was used to monitor oxygen uptake in 500 ml bottles maintained at 25° C. Each 500 ml bottle contained $SSC_3$ minimal salt medium and 20 mM MOPS buffer (pH adjusted to 7.2). Glycerol, 500 ppmv, was added to all bottles. Glycerol was first diluted 50% v/v with deionized water to reduce the viscosity and 0.5 ml was added to each reactor. High molecular weight fatty acids (C-16 and C-18) were weighed individually and added to the appropriate bottles to a 1000 mg/L concentration except for oleic acid, which was tested at 200 mg/L. The low molecular weight fatty acids (C-2, C-4 and C-5) were filter sterilized using chemical resistant filters (0.2 µm) and were added to the appropriate autoclaved bottles to provide 1000 mg/L concentration.

A pure culture of SB3112 was used as inoculum The optical density (OD) of an overnight culture in plate count broth (PCB) was determined in order to estimate the bacterial count. The target dose into each reactor was $1 \times 10^6$ CFU/ml based on the optical density measurement of the broth culture. MacConkey streaks were performed on the inoculum at the time of use to detect Gram-negative contamination. Sterile techniques were used in all experiments.

Treatments (numbers show triplicates as indicated below)

| | |
|---|---|
| 1, 2, 3. | Glycerol only control |
| 4, 5, 6. | C-18 |
| 7, 8, 9. | C-16 |
| 10, 11, 12. | C-5 |
| 13, 14, 15. | C-4 |
| 16, 17, 18. | C-2 |
| 19, 20, 21. | C-18:1 |

(C represents carbon chain length)

MacConkey and standard methods agar (SMA) agar streaks were performed on each bottle's contents at the end of the experiment. The MacConkey agar plates were used to detect Gram-negative contamination. The SMA plates were used to test for pure culture. No contamination was detected.

Oxygen uptake response attributed to the individual fatty acid was calculated by subtracting the glycerol data from the fatty acid plus glycerol data, in order to observe the amount of oxygen uptake attributed to the oxidation of the fatty acid alone. The pH of each reactor at the end of the experiment was within the range of 6.8 to 7.2. Standard Methods Agar (SMA) plates were streaked from each bottle, All bottles showed single colony morphologies on SMA plates at the end of the experiment indicating that pure culture testing was achieved. Final MacConkey streaks of all bottles were negative (no Gram-negative contamination).

Table 3 shows the activity of SB3112 for degrading various fatty acids. The oxygen uptake rates were calculated using a three-point running average and the maximum value is shown in the Table. The results indicate that SB3112 degrades (oxidizes) all these fatty acids (oleic, stearic, palmitic, valeric, butyric and acetic acids). It may be noted that valeric and butyric acids are particularly odorous, and because SB3112 degrades these compounds, SB3112 may be useful in reducing odors attributable to these and similar volatile fatty acids.

Efficacy of SB3112 to Degrade Grease

The following study was performed to show the efficacy of SB3112 to degrade grease.

Respirometer bottles were prepared by adding 250 ml of $SSC_3$ mineral salt media to each bottle. The pH of the medium was adjusted to 7.0 prior to autoclaving. The bottles containing $SSC_3$ media were autoclaved for two hours. Waste kitchen grease was autoclaved separately to kill unwanted microorganisms. Following autoclaving of the grease, 2 ml of the hot sterile grease was added to each cooled 250 ml respirometer bottle. The inoculum for the respirometer bottles was an overnight broth culture (plate count broth) of each strain, or the 9002 blend of microorganisms. Each bottle was inoculated to contain initially≈3× $10^5$ CFU/ml. Following inoculation a caustic trap containing 5 ml of 30% KOH to remove carbon dioxide was suspended in the bottle and the septum cap was secured tightly.

To show superiority of SB3112, a comparative study was performed using two other inoculum samples. Thus, the three inoculum were as follows:

1. *Bacillus megaterium* strain SB3112.
2. Inoculum 9002, representing a blend of four spores (*Bacillus licheniformis, Bacillus amyloliquefaciens, Bacillus pasteurii,* and *Bacillus laevolacticus*) that produce extracellular enzymes lipase, amylase and protease. This mixture is known to affect the degradation of kitchen waste materials, but does not degrade fatty acids.
3. Inoculum SB3012 and SB3013 representing a blend of Gram-negative microorganisms known for their ability to degrade fatty acids.

Following inoculation, the bottles containing the $SSC_3$ media, waste kitchen grease, and the inoculum were placed into the respirometer water bath (23° C.). Each bottle was then connected to a respirometer port. Consumption of oxygen was monitored continuously by the respirometer.

Figure 1:
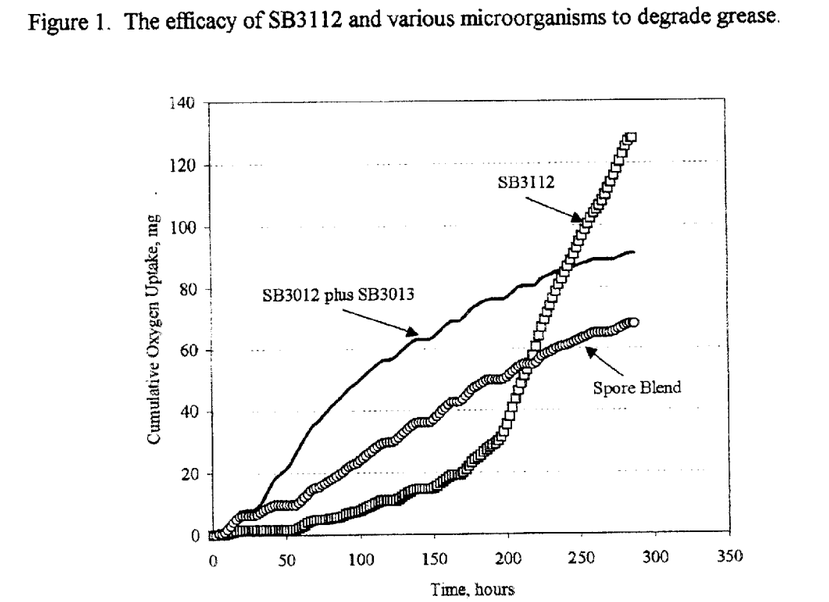
FIG. 1 shows the efficacy of various microorganisms to degrade grease and FIGS. 2 through 7 show the effect of glycerol on biodegrading activity of SB3112 and various microorganisms.

The results of this experiment are shown in FIG. 1. The data show that the Gram-negative microorganism mixture (SB3012 and SB3013) began consuming oxygen almost immediately at a rate of 1.5 mg $O_2$/L/hr. The 9002 spore blend also began consuming oxygen quickly, but the rate of 1.2 mg $O_2$/L/hr was slightly lower than SB3012 and SB3013. Strain SB3112 had a lag of 50 hr before oxygen consumption began at the rate of 0.5 mg $O_2$/L/hr. At about 180 hr, SB3112 began a rapid rise in oxygen consumption surpassing both the spore blend 9002 and the Gram-negative blend. The rate of oxygen consumption by SB3112 after 180 hr was 4.4 mg $O_2$/L/hr compared to 0.7 and 0.8 mg $O_2$/L/hr for SB3012 plus SB3013 and 9002, respectively, during the same time period. Uninoculated controls did not show oxygen uptake (data not shown).

Effect of Glycerol on Biodegrading Activity of SB3112

As shown by the following study, it was discovered that the presence of glycerol enhances the biodegrading activity of SB3112.

SB3112 culture was obtained from retained slant and plated on agar by standard method. A single colony was picked then grown overnight in standard plate count broth. Based on the measured optical density, $1 \times 10^6$ CFU/ml (target) of SB3112 was added to each reactor. Each substrate (stearic acid and glycerol) was added to the reaction vessel prior to autoclaving. The reactor size was 500 ml containing $SSC_3$ autoclaved medium.

Treatments (in duplicate)

1, 2. Stearic acid, 0.2%, 3, 4. Stearic acid, 0.2%+0.1% glycerol 5, 6. Glycerol, 0.1%.

Figure 2:
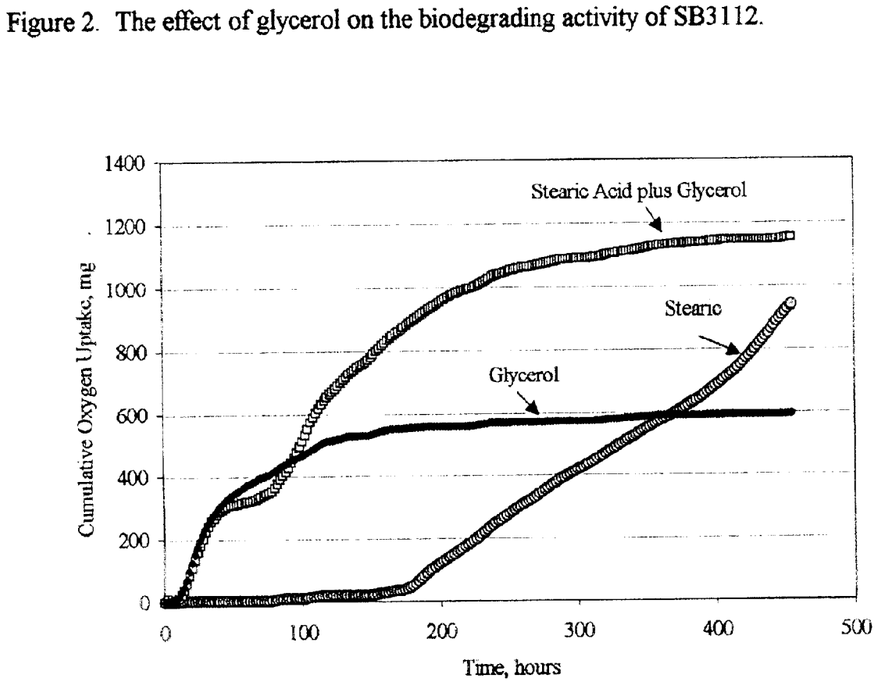

Final MacConkey streaks were performed to detect any Gram-negative contamination. No contamination was found. The results are shown in FIG. 2. The data clearly indicate that fatty acid degrading activity of SB3112 is significantly enhanced by the presence or addition of glycerol.

Comparative Study of Glycerol Level on Fatty Acid Degradation by Various Microorganisms Comparisons of biodegrading activity of various microorganisms as a function of various glycerol levels were performed to show the effect of glycerol as an activator. Long chain fatty acids (LCFA) were used as target substrates and an aqueous serial dilution of glycerol (G) was used to determine the effective concentration range of glycerol as an activator. Measurement of LCFA degradation was determined by the respirometric oxygen uptake and the rate of biodegrading activity of a microorganism was indicated by the rate of oxygen uptake, the methods and materials employed being similar to those described for various experiments herein above. However, the specifics of various studies have been noted for each study set forth below. The *Bacillus megaterium* strains were obtained from ATCC.

Common methods for each of the following experiments:

A CES AER-200 respirometry system was used. The 500 ml respirometer bottles (reactors) contained $SSC_3$ minimal salts medium and 20 mM MOPS adjusted to a pH of 7.2. The target substrates, LCFA, were added as described in the individual experimental methods below.

Glycerol was diluted 50% (w/w) with de-ionized water to reduce the viscosity and then pipetted (v/v) into the appropriate reactor. Reactors were sterilized by autoclaving and sterile techniques were used in each experiment. MacConkey streaks were performed on each inoculum at time of use to detect Gram-negative contamination. MacConkey and standard methods agar (SMA) agar plate streaks were performed on each bottle's contents at the end of the experiment. The SMA plates were used to test for pure cultures.

Specific methods employed in each of the following four studies are detailed below.

Study 1: Glycerol Ladder

This study was undertaken to determine the effective concentration of glycerol for the enhancement of degradation of a LCFA as measured by the increased rate of oxygen uptake.

Specific methods: Palmitic acid was added to each reactor at 500 mg per 500 ml (w/v). Diluted glycerol was added by pipette (v/v) as described in Table 4. A pure culture of SB3112 was used as the inoculum The optical density (OD) of an overnight culture in plate count broth (PCB) was determined in order to estimate the bacterial count. The target dose into each reactor was based on the optical density measurement of the broth culture.

Figure 3:
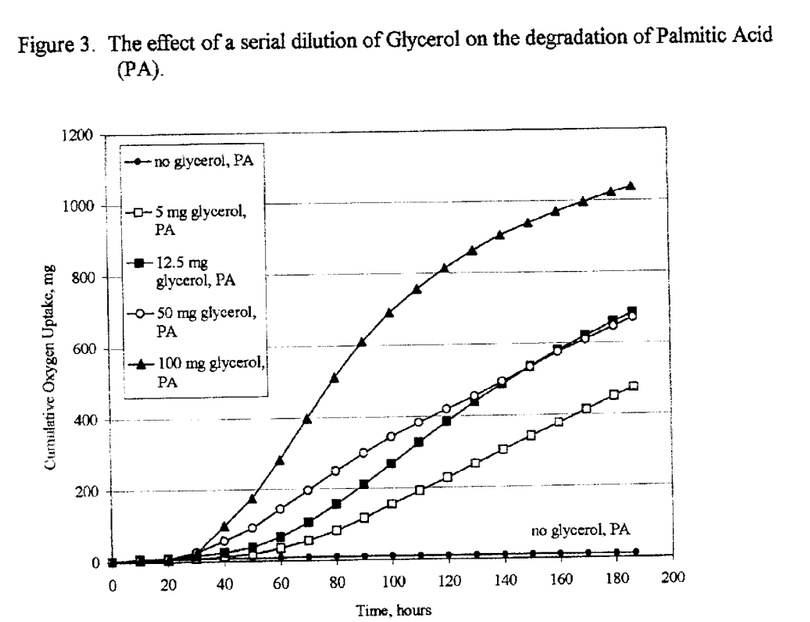

FIG. 3 shows the averaged data as a function of serial dilution of glycerol using palmitic acid as a substrate. All concentrations of glycerol (10 ppm to 200 ppm) showed a significant enhancement of the degradation of palmitic acid. Without the addition of glycerol, no significant oxygen uptake was observed indicating no degradation of palmitic acid.

Figure 4:
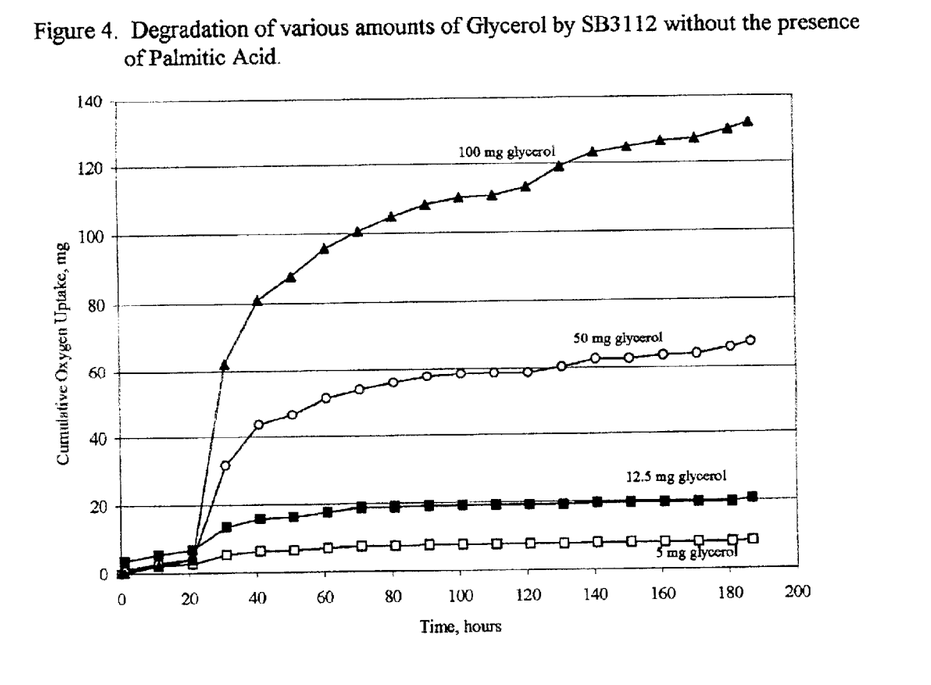
Figure 5:
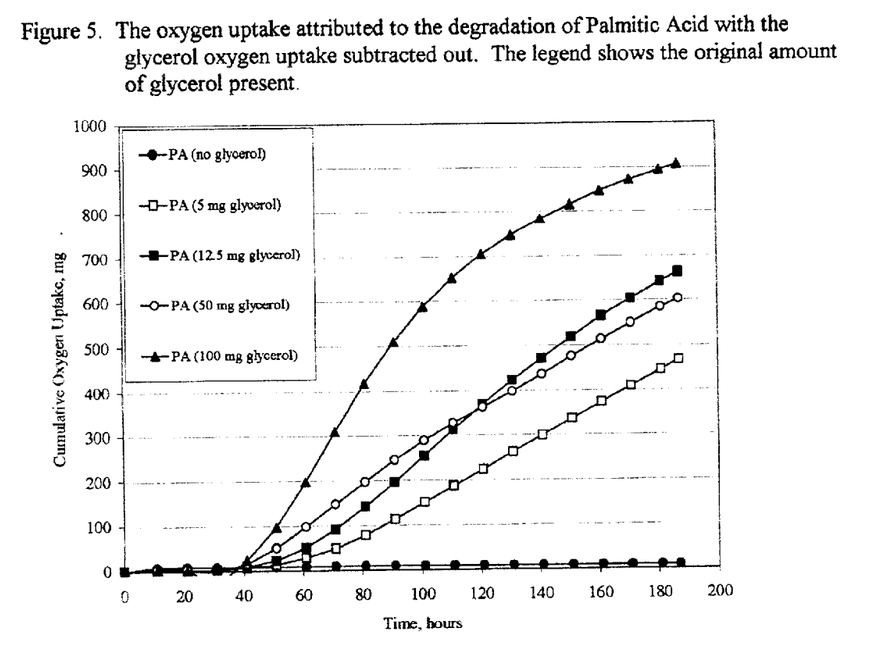

FIG. 4 shows the oxygen uptake as a function of serial addition of glycerol in the absence of palmitic acid. These values were subtracted from the glycerol plus palmitic acid data shown in FIG. 3 (note the differences in the Y axis values between FIGS. 3 and 4). FIG. 5 shows the result of the subtraction and thus shows only the oxygen uptake attributed to the degradation of palmitic acid by SB3112.

It is clear from the data presented that glycerol at a concentration as low as 10 ppm will stimulate the degradation of the LCFA, palmitic acid. It is important to note that glycerol at a concentration of 10 ppm does not produce a significant increase in bacterial cell number Study 2: Other *Bacillus megaterium*

This study was undertaken to compare the effect of glycerol on the degradation of the LCFA, Palmitic acid, using various *Bacillus megaterium* strains.

Specific Methods

Palmitic acid was added 500 mg per 500 ml volume reactor (1000 ppmv). Glycerol was added 50 mg per 500 ml reactor (100 ppmv). Pure culture of each strain was used as the inoculum. The optical density (OD) of an overnight culture in plate count broth (PCB) was determined in order to estimate the bacterial count. The target dose into each reactor was based on the optical density measurement of the broth culture. The treatments for each reactor are shown in Table 5.

Figure 6:
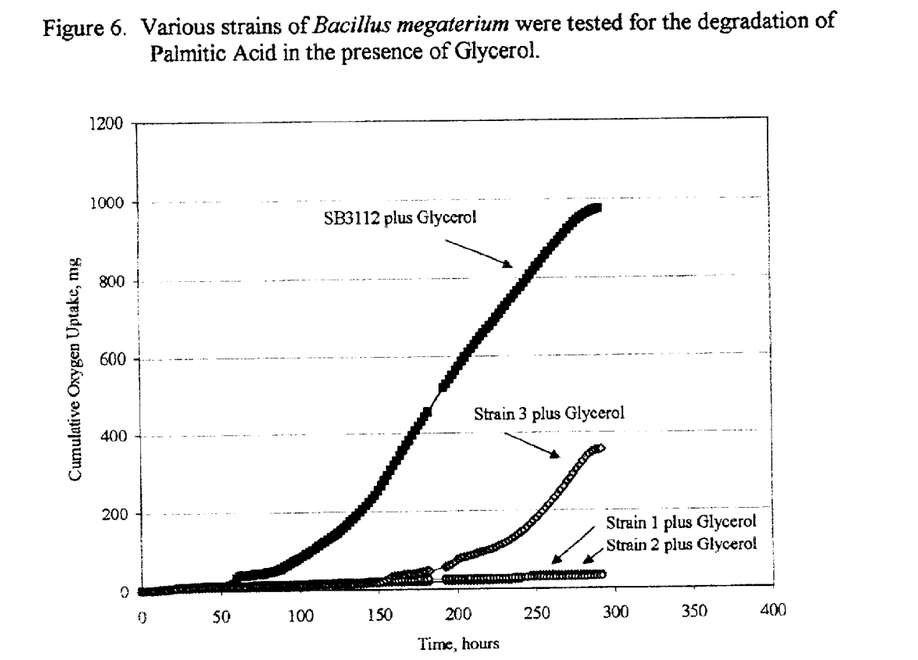

FIG. 6 shows the averaged oxygen uptake data for various *Bacillus megaterium* strains for the degradation of palmitic acid in the presence of glycerol. Strain SB3112 initiated oxygen uptake sooner, produced a high rate of uptake and showed a higher total cumulative oxygen uptake compared to Strain 3. Without the presence of glycerol there was no degradation of palmitic acid in this study as indicated by the absence of oxygen uptake.

The ATCC strains 2 and 1 showed no oxygen uptake on palmitic acid alone or on palmitic acid with the addition of glycerol. In fact, the degradation of glycerol was inhibited in the presence of PA. The amount of oxygen uptake expected from 50 mg of glycerol should be approximately 70 mg.

In short, SB3112 degraded palmitic acid to a much greater extent than strain 3 with the addition of glycerol. ATCC strains 2 and 1 did not degrade palmitic acid with or without glycerol.

Study 3: Other Species of Bacteria

This study was undertaken to compare a commercially available product containing a Gram-positive mixture of 5 to 7 strains with the fully formulated product of the present invention containing SB3112. All strains were in spore form including the SB3112.

Specific Methods are as Follows

The fully formulated products were diluted into the appropriate reactor to achieve an initial spore count in the reactors of about $5.4 \times 10^4$ CFU/ml. The treatments for each reactor are shown in Table 6.

Figure 7:
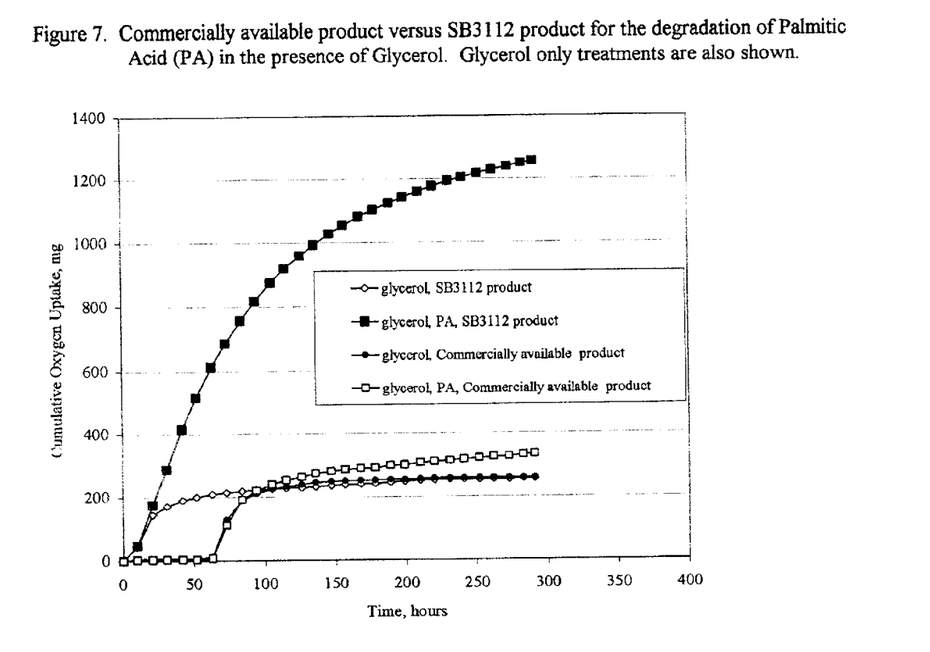

FIG. 7 shows the response to the addition of glycerol to LCFA substrate by the two products. The data indicate that whereas SB3112 containing product readily consumed the palmitic acid, the commercially available mixture did not significantly degrade the palmitic acid. All products and reactors were free of Gram-negative contamination as indicated by no growth when streaked on MacConkey agar.

The data indicate that the product containing SB3112 degraded the palmitic acid whereas the commercially available product did not significantly degrade the palmitic acid. Both products were able to degrade glycerol in the presence of the LCFA.

Study 4: Effect of Glycerol on Biodegradation

This study was undertaken to demonstrate the effect of glycerol on oxidation of fatty acids of various chain lengths.

Specific methods are as follows: Respirometry was used to test each of a number of carboxylic acids ranging in chain length from 2 (acetic acid) to 18 (oleic acid). 1000 mg/L of each acid was tested except oleic which was tested at 200 mg/L. Glycerol was used at a concentration of 500 ppm. The study was conducted for a period of 10 days.

Table 7 shows the utilization of long chain fatty acids by SB3112 spores in the presence of glycerol (glycerol uptake subtracted out). When compared with the data in the absence of glycerol the results obtained in the presence of glycerol demonstrate that glycerol significantly enhances degradation of long-chain (fatty) acids.

Various embodiments of the present invention have now been described in accordance with the objects and advantages noted above. It will be appreciated that these examples are merely illustrative and not limiting of the invention. Of course, many variations and modifications of the present invention will be apparent and suggested to those of ordinary skill in the art and all such variations and modifications are included within the purview and scope of the clam.

TABLE 1

Example Components
in a Liquid Composition according to present invention.

| Component | Quantity Range | Preferred Amount |
|---|---|---|
| Surfactants | | |
| Linear Alkylbenzene Sulphonic Acid | 0.5–5% | 1–2% |
| Ethoxylated alcohol | 0.5–5% | 0.5–1.5% |

TABLE 1-continued

Example Components in a Liquid Composition according to present invention.

| Component | Quantity Range | Preferred Amount |
|---|---|---|
| Preservatives | | |
| 1,2-benzisothiazolin-3-one | 0.025–0.2% | 0.045–0.1% |
| Methyl anthranilate | 20–40 ppm | 25–35 ppm |
| Microorganisms | | |
| Bacillus licheniformis | $1 \times 10^6$ to $1 \times 10^9$ CFU/ml | $5 \times 10^6$ to $1 \times 10^8$ CFU/ml |
| Bacillus amyoliquefaciens | $1 \times 10^6$ to $1 \times 10^9$ CFU/ml | $5 \times 10^6$ to $1 \times 10^8$ CFU/ml |
| Bacillus pasteurii | $1 \times 10^6$ to $1 \times 10^9$ CFU/ml | $5 \times 10^6$ to $1 \times 10^8$ CFU/ml |
| Bacillus laevolacticus | $1 \times 10^6$ to $1 \times 10^9$ CFU/ml | $5 \times 10^6$ to $1 \times 10^8$ CFU/ml |
| Activator | | |
| Glycerol | 0–10% | 0.001%–4% |
| Other ingredients | | |
| Tetrasodium ethylenediamine tetraacetate (stabilizer) | 0.1–1.0% | 0.2–0.5% |
| Fragrance | 0–0.5% | 0.2–0.3% |
| Other spore forming microorganisms | 0 to $1 \times 10^9$ CFU/ml | $5 \times 10^6$ to $1 \times 10^8$ CFU/ml |
| Viscosifier | 0–0.5% | 0.2–0.3% |

TABLE 2

Stearic acid utilization by various *Bacillus megaterium* strains.

| Parameter | SB3112 | Strain 1 | Strain 2 | Strain 3 |
|---|---|---|---|---|
| Lag phase (hours) | 20 | 72 | 60 | 100 |
| Oxygen uptake rate (mg/hr) | 1.9 | 1.1 | 0.8 | 0.9 |
| Total cumulative oxygen uptake (mg) | 180 | 140 | 110 | 90 |

Each reactor volume was 0.5 liters.

TABLE 3

Degradation of fatty acids by *Bacillus megaterium* strain SB3112.

| Fatty acid used | Oxygen uptake rate (mg/hr) | Total cumulative oxygen uptake (mg) |
|---|---|---|
| oleic acid, C-18:1 | 4.9 | 185 |
| stearic acid, C-18 | 1.75 | 230 |
| palmitic acid, C-16 | 2.87 | 480 |
| valeric acid, C-5 | 2.37 | 342 |
| butyric acid, C-4 | 1.96 | 308 |
| acetic acid, C-2 | 1.7 | 247 |

Each reactor volume was 0.5 liters. Oleic acid was 100 mg per reactor and all other substrates were 500 mg per reactor.

TABLE 4

Glycerol Ladder Treatments.

| Reactor | Glycerol, ppm | Palmitic acid (500 mg per reactor) | volume of diluted glycerol per 500 ml reactor |
|---|---|---|---|
| 1, 2, 3. | No glycerol | yes | 0 |
| 4, 5. | 10 ppm | yes | 10 μl |
| 6, 7. | 25 ppm | No | 25 μl |
| 8, 9, 10. | 25 ppm | yes | 25 μl |
| 11, 12. | 100 ppm | No | 100 μl |
| 13, 14, 15. | 100 ppm | yes | 100 μl |
| 16, 17. | 200 ppm | No | 0.20 ml |
| 18, 19, | 200 ppm | yes | 0.20 ml |

TABLE 5

Other *Bacillus megaterium* Treatments.

| Reactor | Glycerol, ppm | Strain |
|---|---|---|
| 1, 3 | No glycerol | SB3112 |
| 4, 5. | 100 ppm | SB3112 |
| 6, 7. | No glycerol | Strain 2 |
| 8, 9. | 100 ppm | Strain 2 |
| 14, 15. | No glycerol | Strain 1 |
| 16, 17. | 100 ppm | Strain 1 |
| 22, 23. | No glycerol | Strain 3 |
| 24. | 100 ppm | Strain 3 |

TABLE 6

Other species of bacteria Treatments

| Reactor # | Palmitic acid | Product |
|---|---|---|
| 1, 2, 3 | Yes | Commercially available product |
| 4, 5, 6 | Yes | SB3112 product |
| 7, 8 | No | Commercially available product |
| 9, 10 | No | SB3112 product |

TABLE 7

Growth rates of SB3112 on various carboxylic acids.

| | With Glycerol* | | Without Glycerol*** | |
|---|---|---|---|---|
| Fatty acid | Oxygen uptake rate (mg/L/hr) | Total cumulative oxygen uptake (mg/L) | Oxygen uptake rate (mg/L/hr) | Total cumulative oxygen uptake (mg/L) |
| oleic acid**, C-18:1 | 9.8 | 370 | 0 | 0 |
| stearic acid, C-18 | 3.5 | 460 | 0 | 0 |
| palmitic acid, C-16 | 5.7 | 960 | 0 | 0 |

*Glycerol uptake subtracted out
**Oleic acid was 200 mg per reactor while stearic and palmitic were 500 mg per 500 ml reactor.
***No uptake was measured for the above fatty acids prior to 150 hours of treatment without the presence of glycerol.

What is claimed is:

1. A method for degrading fatty acid or grease, comprising exposing fatty acid, grease, or fatty acid and grease to a composition comprising *Bacillus megaterium* strain SB3112 having all of the characteristics of ATCC deposit number PTA-3142.

2. The method of claim 1, comprising adding a biodegrading activator to the composition.

3. The method of claim 2, wherein the activator is glycerol in a range of about 0.001% to about 10% (v/v).

4. The method of claim 1, comprising adding a surfactant to the mixture to enhance bioavailability of fatty acids and grease.

* * * * *